United States Patent [19]

Beck

[11] Patent Number: 5,086,172

[45] Date of Patent: Feb. 4, 1992

[54] PREPARATION OF 2,4,6-TRICYANO-1,3,5-TRIAZINE

[75] Inventor: Gunther Beck, Leverkusen, Fed. Rep. of Germany

[73] Assignee: Bayer Aktiengesellschaft, Leverkusen, Fed. Rep. of Germany

[21] Appl. No.: 637,386

[22] Filed: Jan. 3, 1991

[30] Foreign Application Priority Data

Jan. 10, 1990 [DE] Fed. Rep. of Germany ....... 4000480

[51] Int. Cl.$^5$ ............................................ C07D 251/24
[52] U.S. Cl. .................................................. 544/180
[58] Field of Search ........................................ 544/180

[56] References Cited

PUBLICATIONS

Carrington et al., Chemical Abstracts, vol. 64, entry 195e (1966).

Primary Examiner—John M. Ford
Attorney, Agent, or Firm—Sprung Horn Kramer & Woods

[57] ABSTRACT

A process for the preparation of 2,4,6-tricyano-1,3,5-triazine, comprising reacting a 2,4,6-trihalogeno-1,3,5-triazine of the formula

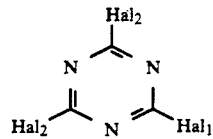

in which
$Hal_1$ and $Hal_2$ independently of one another represent chlorine or fluorine, with an alkali metal cyanide or an alkaline earth metal cyanide.

7 Claims, No Drawings

PREPARATION OF 2,4,6-TRICYANO-1,3,5-TRIAZINE

The invention relates to a new process for the preparation of 2,4,6-tricyano-1,3,5-triazine (cyanuric cyanide).

2,4,6-Tricyano-1,3,5-triazine is an interesting chemical compound; for example, it forms electrically-conducting charge transfer complexes with tetrathiafulvalene (see Synthetic Metals 19, page 415 (1987)). In addition, the compound reacts on treating with methanol under certain conditions with the formation of 2-cyano-4,6-dimethoxy-1,3,5-triazine (Chem. Ber. 52, 659 (1919)), which, for its part, is a useful intermediate for the production of highly effective herbicides (see EP-A 0,094,260).

However, until now there has still been no process available by which 2,4,6-tricyano-1,3,5-triazine can be prepared in relatively large amounts. The only process described until now for the preparation of the compound consists in heating 2,4,6-triscarboxamido-1,3,5-triazine with phosphorus pentoxide and sand (see Tetrahedron (1963) 19, pages 161 to 167, in particular page 162 and page 166).

However, the 2,4,6-triscarboxamido-1,3,5-triazine required as a starting compound must in turn be prepared from diethyl oxalate in a complicated four-step process. The yields of pure 2,4,6-tricyano-1,3,5-triazine based on the triscarboxamidotriazine are only between 12 to 17% of theory, i.e. the process is not suitable for preparation of relatively large amounts of the desired tricyanotriazine.

It has now been found that the desired 2,4,6-tricyano-1,3,5-triazine can be obtained in a simple manner starting from inexpensive starting materials by reaction of alkali metal cyanides or alkaline earth metal cyanides with 2,4,6-trihalogeno-1,3,5-triazines of the formula

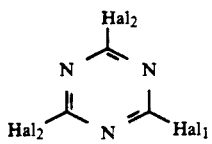

in which $Hal_1$ and $Hal_2$ independently of one another represent chlorine or fluorine.

The invention therefore relates to a process for the preparation of 2,4,6-tricyano-1,3,5-triazine, which is characterized in that 2,4,6-trihalogeno-1,3,5-triazines of the formula (I) are reacted with alkali metal cyanides or alkaline earth metal cyanides.

It has been found that 2,4,6-tricyano-1,3,5-triazine is obtained in good yields and high purity from 2,4,6-trihalogeno-triazines of the formula.(I), preferably from 2,4,6-trichloro-1,3,5-triazine (cyanuric chloride) or 2,4,6-trifluoro-1,3,5-triazine (cyanuric fluoride) in a simple one-step reaction if the trihalogenotriazines of the formula (I) are reacted with alkali metal cyanides or alkaline earth metal cyanides in certain solvents and under mild reaction conditions and alkali metal cyanides and alkaline earth metal cyanides are used in not more than a small excess over the amount stoichiometrically required for the reaction. By means of the parameters "mild reaction conditions" and "not more than a small excess of alkali metal cyanides or alkaline earth metal cyanides", the formation of undesired secondary products, which are prominent owing to the high reactivity of the tricyanotriazine, is so largely suppressed that the desired tricyanotriazine is still obtained in good yields.

The invention therefore relates in particular to a process for the preparation of 2,4,6-tricyano-1,3,5-triazine, which is characterized in that 2,4,6-trihalogeno-1,3,5-triazines of the formula (I) are reacted in aliphatic or cyclic ethers or aliphatic nitriles under mild reaction conditions with not more than a small excess over the stoichiometrically required amount of alkali metal cyanides or alkaline earth metal cyanides.

Of the aliphatic and cyclic ethers and aliphatic nitriles to be used as specific solvents according to the invention, diethylene glycol dimethyl ether (diglyme), 1,2-dimethoxyethane, tetrahydrofuran, propionitrile and acetonitrile have proved particularly suitable. Acetonitrile is particularly preferably used.

Alkali metal cyanides and alkaline earth metal cyanides which are preferably used are the inexpensive alkali metal cyanides sodium cyanide and potassium cyanide.

In order to replace the three halogen atoms in the cyanuric halides of the formula (I), 1.5 moles of alkaline earth metal cyanide or 3 moles of alkali metal cyanide are necessary per mole of trihalogeno-triazine.

According to the invention, not more than a small excess of at most 20 mole-% relative to the molar amount theoretically required for the complete reaction of the halogen atoms is used. However, it has been found that it can be highly advantageous to work with a subequivalent amount of cyanides; a part of the trihalogenotriazine corresponding to the subequivalent amount then in fact remains unreacted; however, as tricyanotriazine can be separated in a simple manner from, for example, unreacted trifluorotriazine and this recovered trihalogenotriazine can be used again in the next batch, and through the use of a subequivalent amount of cyanide the secondary product formation is reduced, it can be highly efficient to use substantially less than the amount of cyanide stoichiometrically required in the process according to the invention. Very generally, 0.3 to 3.6 equivalents of alkali metal cyanide or alkaline earth metal cyanide are employed per mole of trihalogenotriazine in the process according to the invention.

The reaction, according to the invention, of the trihalogenotriazines of the formula (I) with the alkali metal cyanides or alkaline earth metal cyanides actually proceeds, as can be determined with gas chromatographic monitoring of the reaction, via the monocyano-dihalogeno and dicyano-monohalogeno-1,3,5-triazine intermediates; in spite of this, essentially only the 2,4,6-tricyano-1,3,5-triazine is formed even on using a subequivalent amount of cyanide if the reaction is carried out to its completion.

The reaction, according to the invention, of the trihalogenotriazines with the alkali metal cyanides and alkaline earth metal cyanides can be described by the following reaction equation:

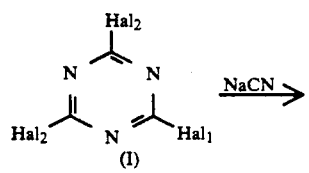

-continued

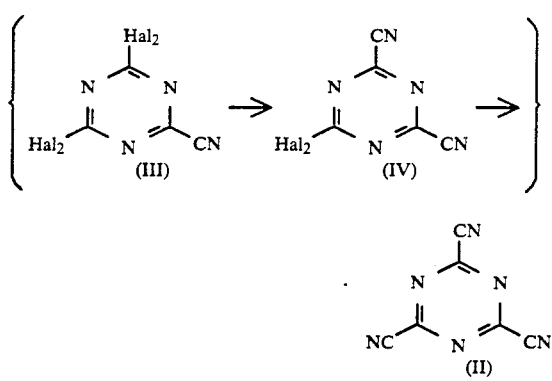

Monocyanodihalogeno-1,3,5-triazine (III) and dicyanomonohalogeno-1,3,5-triazine (IV) can above all be isolated and detected by gas chromatography if the reaction according to the invention is carried out with a subequivalent amount of cyanides and prematurely discontinued. The retention times of (III) and (IV) are between the retention times of (I) and (II) in the gas chromatogram.

The reaction according to the invention is carried out under mild conditions, i.e. at temperatures of −50° to +80° C., preferably at −40° to +50° C. and particularly preferably at −30° to +30° C. The temperature depends on the trihalogeno-triazine used; the extremely reactive cyanuric fluoride requires lower reaction temperatures, and the somewhat slower-reacting cyanuric chloride requires somewhat higher reaction temperatures. The course of the reaction can be monitored by gas chromatography. The reaction is complete as soon as the composition of the reaction mixture no longer changes according to the gas chromatogram. The reaction times to this completion of the reaction vary between 1 and 200 hours, depending on the trihalogeno-triazine, batch size and reaction temperatures.

The reaction according to the invention is preferably carried out such that the total amount of cyanide intended for the reaction is added either in portions or immediately to the solution of the trihalogenotriazine in the relevant anhydrous solvent at temperatures of −30° to +30° C. with stirring and the temperatures of the reaction mixture is slowly allowed to rise with stirring to the intended final temperature.

The working-up of the reaction mixture is preferably carried out by separating off the alkali metal halides and alkaline earth metal halides (chlorides or fluorides) mechanically, for example by filtration, freeing the filtrate of solvent in vacuo and immediately isolating the tricyanotriazine from the residue by sublimation (for example at 100° to 110° C./0.1 mbar) or by recrystallization, for example from benzene. However, it has proved more advantageous first to treat the residue with a solvent in which the tricyanotriazine is soluble but in which the undesired secondary products are virtually insoluble. Solvents of this type are, for example, di- or trichloromethane. After separating off the substances insoluble in the solvent and concentrating the filtrate in vacuo, an already virtually pure tricyanotriazine is obtained. This can be still further purified, if desired, by recrystallization and/or sublimation. As, for example, cyanuric chloride is clearly more easily soluble in benzene than tricyanotriazine, unreacted cyanuric chloride can be removed by recrystallization from benzene or by chromatography.

EXAMPLES

Example 1

152 g (3.1 mol) of sodium cyanide are added with stirring and with exclusion of moisture to a solution, cooled in an ice bath to 0° to 5° C., of 184.4 g (1 mol) of cyanuric chloride in 2,500 ml of anhydrous acetonitrile. The reaction mixture is vigorously stirred for about 70 hours, initially with ice bath cooling for about 12 hours and then at room temperature.

The reaction mixture is worked up with the exclusion of atmospheric moisture as follows: The residue is filtered off and concentrated to dryness in vacuo in a rotary evaporator at room temperature. The oily residue is stirred vigorously with anhydrous dichloromethane (about 1 l) at room temperature. After filtering off undissolved material, the filtrate is concentrated to dryness in a rotary evaporator, first at room temperature, then at 30° C. The residual crude 2,4,6-tricyano-1,3,5-triazine (109 g=70% of theory) in the form of a dry, crystalline brownish powder is obtained in the form of pure white crystals by sublimation at 100° to 110° C./0.1 mbar.

Yield: 92.7 g (=59.4% of theory).

IR (KBr) in cm$^{-1}$: 2276, 2255, 1653, 1555, 1515, 1339, 939, 822.

The positions of the absorption bands essentially agree with the data in the literature (measured in Nujol; Tetrahedron 19, 161–167 (1973).

Example 2

The solution obtained from 36.9 g (0.2 mol) of cyanuric chloride in 750 ml of anhydrous acetonitrile was reacted with 32.34 g (0.66 mol) of sodium cyanide under the reaction conditions described in Example 1. Gas chromatographic analysis of the reaction mixture showed that cyanuric chloride was no longer present after 45 hours. The reaction mixture was worked up as described in Example 1.

Yield of pure 2,4,6-tricyano-1,3,5-triazine: 14.0 g (=44.9% of theory).

Example 3

13.97 g (0.215 mol) of potassium cyanide are added at room temperature with vigorous stirring and with the exclusion of moisture to the solution obtained from 12.0 g (0.065 mol) of cyanuric chloride in 250 ml of anhydrous acetonitrile; the reaction mixture initially warms to 35°–40° C. in this case.

The gas chromatographic analysis of the reaction mixture showed a ratio of cyanuric chloride to 2,4,6-tricyano-1,3,5-triazine such as, for example., 1:99 after 24 hours. After stirring for a further 24 hours, cyanuric chloride was no longer detectable.

The reaction mixture was worked up as described in Example 1.

Yield of pure 2,4,6-tricyano-1,3,5-triazine: 4.5 g (=44.4% of theory).

Example 4

4.9 g (0.1 mol) of sodium cyanide are added with stirring and with exclusion of moisture to a solution, cooled to −35° C., of 27.0 g (0.2 mol) of cyanuric fluoride in 500 ml of anhydrous acetonitrile. After removal of the cooling bath, the temperature of the reaction mixture rises to 0° C. in the course of about 1 hour. The temperature of the reaction mixture is kept at 0° C. for about 8 hours by means of an ice bath. The temperature of the reaction mixture is then gradually allowed to rise to 13° C. in the course of a further 13 hours.

The reaction mixture is then concentrated to dryness in a rotary evaporator and the residue is vigorously stirred with dichloromethane (about 250 ml). After filtering off undissolved material, the filtrate is concentrated in a rotary evaporator at room temperature; the last residues of dichloromethane and cyanuric fluoride are removed by applying a high vacuum.

Yield of crude 2,4,6-tricyano-1,3,5-triazine: 4.25 g (=81.7% of theory relative to sodium cyanide employed); the crude product is purified by sublimation at 120° C./0.1 mbar;

Yield of pure 2,4,6-tricyano-1,3,5-triazine: 4.11 g (=79% of theory, relative to sodium cyanide employed).

The gas chromatographic and mass spectroscopic analysis following this (GC-MS analysis) of the reaction mixture showed that at the start of the reaction, i.e. after the reaction mixture had been stirred at 0° C. for about 2 hours, the two intermediates 2-cyano-4,6-difluoro-1,3,5-triazine and 2,4-dicyano-6-fluoro-1,3,5-triazine were present in the reaction mixture.

Example 5

7.35 g (0.15 mol) of sodium cyanide were added with stirring and with exclusion of moisture to a solution, cooled to 1° to 3° C. in an ice bath, of 27.66 g (0.15 mol) of cyanuric chloride in 500 ml of anhydrous acetonitrile. The reaction mixture was vigorously stirred, first in an ice bath for about 10 hours, then at about 15° C. for about 110 hours. The composition of the reaction mixture was determined by means of GC-MS after 24 hours, after 48 hours and after 120 hours; the following contents of cyanuric chloride, tricyanotriazine, dichloromonocyanotriazine and monochlorodicyanotriazine resulted in this way.

| Time [h] | Cl-triazine-Cl,Cl | Cl-triazine-Cl,CN | Cl-triazine-CN,CN | CN-triazine-CN,CN |
|---|---|---|---|---|
| 24 | 61.1% | 4.4% | 1.1% | 32.9% |
| 48 | 60.5% | 3.8% | 0% | 35.7% |
| 120 | 62.3% | 3.8% | 0% | 33.9% |

The reaction mixture was worked up as described in Example 1.

Yield of pure tricyanotriazine after recrystallization from benzene: 41% of theory, relative to sodium cyanide employed.

Example 6

The reaction was carried out as described in Example 1 with the sole difference that the reaction mixture was stirred at 0° to 5° C. for 140 hours.

Yield of sublimed 2,4,6-tricyano-1,3,5-triazine: 89.9 g (=57.6% of theory).

Example 7

15.5 g (0.316 mol) of sodium cyanide are added to the solution obtained from 18.44 g (0.1 mol) of cyanuric chloride in 400 ml of anhydrous tetrahydrofuran and the mixture is vigorously stirred at room temperature with exclusion of moisture for 120 hours. According to GC analysis, cyanuric chloride is then no longer present in the reaction mixture.

The reaction mixture is worked up as described in Example 1.

Yield of pure sublimed 2,4,6-tricyano-1,3,5-triazine: 7.09 g (=45.4% of theory).

Example 8

The reaction was carried out as described in Example 1 with the sole difference that instead of 152 g (3.1 mol) of sodium cyanide there were added only 142 g (2.9 mol) of sodium cyanide. The reaction time was about 120 hours.

Yield of purest 2,4,6-tricyano-1,3,5-triazine after sublimation: 94.1 g (=60.3 % of theory).

There are obtained comparable yields of 2,4,6-tricyano-1,3,5-triazine, when 1,2-dimethoxyethane is employed as solvent instead of acetonitrile.

It will be understood that the specification and examples are illustrative but not limitative of the present invention and that other embodiments within the spirit and scope of the invention will suggest themselves to those skilled in the art.

What is claimed is:

1. A process for the preparation of 2,4,6-tricyano-1,3,5-triazine, comprising reacting a 2,4,6-trihalogeno-1,3,5-triazine of the formula

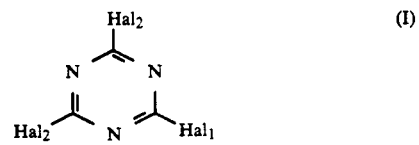

in which
Hal$_1$ and Hal$_2$ independently of one another represent chlorine or fluorine, with an alkali metal cyanide or an alkaline earth metal cyanide.

2. The process according to claim 1, wherein the reaction is effected in an aliphatic or cyclic ether or an aliphatic nitrile with at most about a 20% excess over the stoichiometrically required amount of the alkali metal cyanide or alkaline earth metal cyanide.

3. The process according to claim 2, wherein about 0.3 to 3.6 equivalents of alkali metal cyanide or alkaline earth metal cyanide are used per mole of 2,4,6-trihalogeno-1,3,5-triazine.

4. The process according to claim 2, wherein the reaction is carried out at a temperature of about −50° to −80° C.

5. The process according to claim 2, wherein the reaction is carried out at a temperature of about −40° to 50° C.

6. The process according to claim 2, wherein the reaction is carried out at a temperature of about −30° to +30° C.

7. The process according to claim 3, wherein the reaction is carried out at a temperature of about −30° to +30° C.

* * * * *

UNITED STATES PATENT AND TRADEMARK OFFICE
CERTIFICATE OF CORRECTION

PATENT NO. : 5,086,172

DATED : February 4, 1992

INVENTOR(S) : Gunther Beck

It is certified that error appears in the above-identified patent and that said Letters Patent is hereby corrected as shown below:

Col. 6, line 59   Delete " $-80^\circ C$ " and substitute -- $+80^\circ C$ --

Col. 6, line 62   Delete " $50^\circ C$ " and substitute -- $+50^\circ C$ --

Signed and Sealed this

Thirteenth Day of July, 1993

Attest:

MICHAEL K. KIRK

Attesting Officer    Acting Commissioner of Patents and Trademarks